United States Patent [19]

Huber et al.

[11] Patent Number: 5,431,789
[45] Date of Patent: Jul. 11, 1995

[54] DETERMINATION OF ORGANIC COMPOUNDS IN WATER

[75] Inventors: Calvin O. Huber, Mequon; Ben S. Hui, Milwaukee, both of Wis.

[73] Assignee: Board of Regents of the University of Wisconsin System of behalf of the University of Wisconsin-Milwaukee, Milwaukee, Wis.

[21] Appl. No.: 13,474

[22] Filed: Jan. 29, 1993

Related U.S. Application Data

[63] Continuation-in-part of Ser. No. 737,219, Jul. 29, 1991, abandoned.

[51] Int. Cl.$^6$ .............................. G01N 27/26
[52] U.S. Cl. ..................... 204/153.14; 204/153.15; 204/153.2; 204/400; 204/412
[58] Field of Search ............. 204/153.1, 400, 402

[56] References Cited

U.S. PATENT DOCUMENTS

| | | | |
|---|---|---|---|
| 2,898,282 | 8/1959 | Flook et al. | 204/153.16 |
| 3,155,603 | 11/1964 | Hart | 204/402 |
| 3,523,883 | 8/1970 | Waclawik et al. | 204/402 |
| 4,201,647 | 5/1980 | Spaziante et al. | 204/402 |
| 4,566,949 | 1/1986 | Berger | 204/402 |
| 4,652,359 | 3/1987 | Niedrach et al. | 204/402 |
| 4,655,900 | 4/1987 | Neti et al. | 204/402 |

FOREIGN PATENT DOCUMENTS

| | | | |
|---|---|---|---|
| 2849480 | 5/1979 | Germany | 204/402 |
| 1531761 | 11/1978 | United Kingdom | 204/402 |

OTHER PUBLICATIONS

Hackh's Chemical Dictionary, 4th ed., 1969, p. 687.
Hui, "Analytica Chimica Acta", 197, (1987), pp. 361–365.
Faraday Society, Transactions, 52, (1956), pp. 1260–1281.
Conway et al, "The Electrochemical Behavior of the Nickel–Nickel Oxide Electrode", *Can. J. Chem.*, vol. 37, (1959), pp. 292–307.
Burke et al, "The Influence of Material Dispersion on the Redox Behavior of Nickel Oxide Electrodes", *J. of Power Sources*, 12 (1984), pp. 203–218.
"Proceedings of the Symposium on the Nickel Electrode", The Electrochemical Soc., Inc., vol. 82-4, pp. 1–19, (1981).
Fleischmann et al, "The Kinetics and Mechanism of the Oxidation of Amines and Alcohols at Oxide–covered Nickel, Silver, Copper and Cobalt Electrodes", J.C.S. Perkin II, pp. 1396–1403, (1972).
Carpenter et al, "The Electrochromic Properties of Hydrous Nickel Oxide", *Solar Energy Materials*, 16, (1987), pp. 333–346.

*Primary Examiner*—T. Tung
*Attorney, Agent, or Firm*—Irving D. Ross, Jr.

[57] ABSTRACT

A method for determining concentrations of solutes such as alcohols, amino acids, carbohydrates, calcium, etc. in water solution. The open-circuit potential shift of an oxidatively pretreated nickel electrode in alkaline solution is used.

4 Claims, 3 Drawing Sheets

PRETREAT /POTENTIOMETER /TIMER

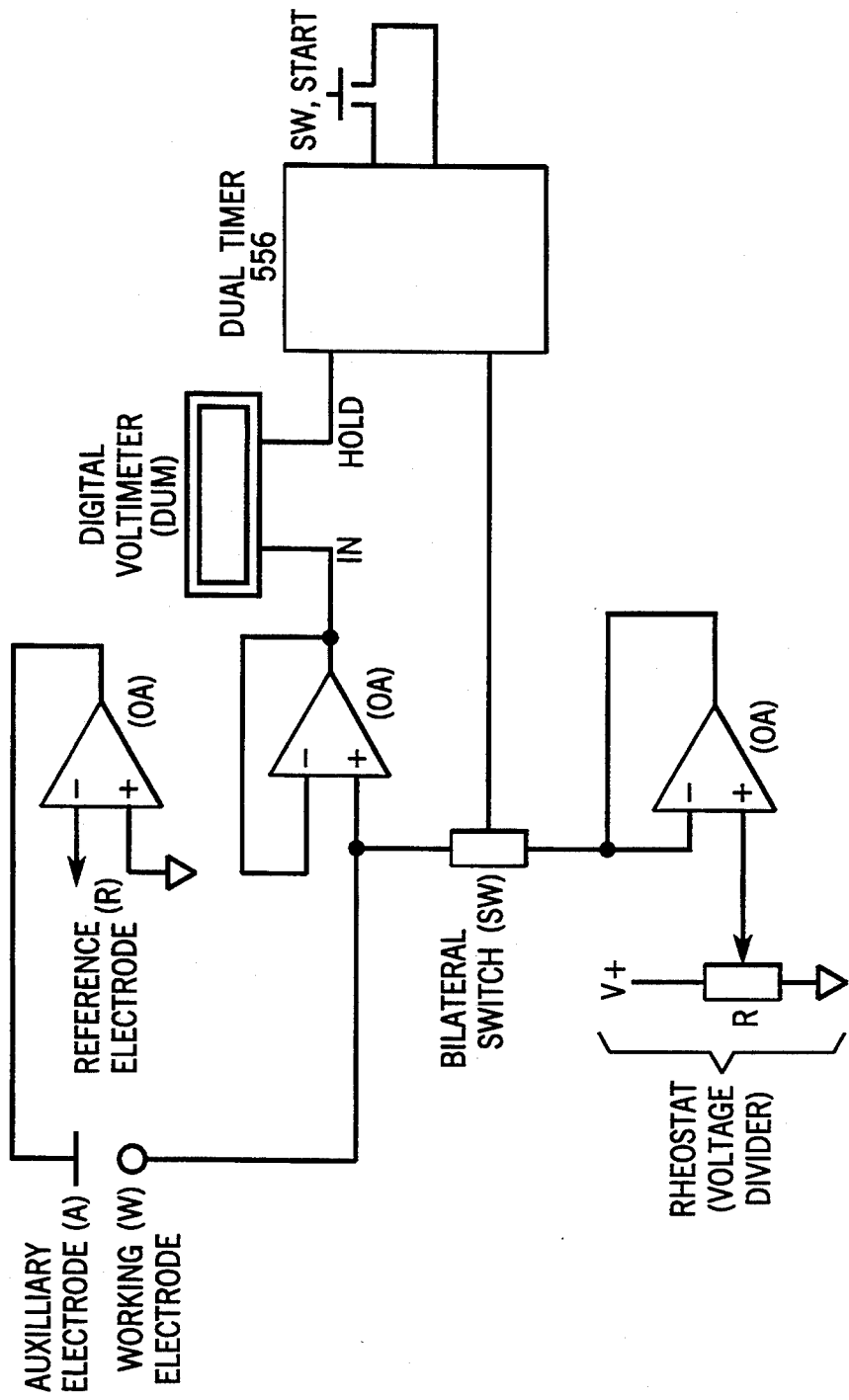
FIG. 3 PRETREAT/POTENTIOMETER/TIMER

DETERMINATION OF ORGANIC COMPOUNDS IN WATER

This invention disclosure is a Continuation-In-Part of prior patent application Ser. No. 07/737,219 which was filed on Jul. 29, 1991, now abandoned.

FIELD OF INVENTION

This invention relates to a method for determining concentrations of solutes in water solution and an instrument to perform that method. Representative of the solutes which can be so determined are oxidizable organics such as alcohols and amines, proteins, and oxidizable inorganics. Calcium in solution can also be determined.

BACKGROUND OF INVENTION

The need for rapid and direct determination of oxidizable solutes in water is evident by comparison to the well known and frequently used indirect biological oxygen demand (BOD) method which ordinarily requires five days and the chemical oxygen demand (COD) method which requires about two hours. These two methods, though widely used, are slow, indirect, and not entirely interchangeable as to results obtained.(1) Another evidence of the importance for such measurements is the total organic carbon method which is based on combustion or high temperature or uv-radiative exhaustive oxidation of organics followed by infrared absorption determination of the carbon dioxide produced.(1)

(1) Standard Methods for the Examination of Water and Wastewater, M. H. Franson (Ed.), Am. Public Health Assoc., Washington, DC, 1989, pp 5-1 to 5-18.

It is an object of this invention to provide an analytical technique and instrument in which pretreatment of a working electrode consisting of a metal that has an oxide surface of that metal on its surface, the timing of both the pretreatment and the monitoring mode, the monitoring of the open circuit potential, and the holding of the final potential for recording are performed in less than two minutes so that direct, rapid, and convenient determinations can be performed with minimal operator training. Although there are numerous reports on the potentiostatic and potentiodynamic responses of nickel oxide electrodes (2), no reports were found on the analytical applications of the potentiometric response of an anodically pre-treated nickel oxide electrode in alkaline electrolyte. Potentiometry offers simplicity in instrumentation and data handling. There are often fewer interferences from mass transport, charging current, and electrolytic reaction processes.

(2) Hui, B. and Huber, C. O., Anal. Chim. Acta, 243, (1991) 279–285.

SUMMARY OF THE INVENTION

The method of this invention in the preferred embodiment consists of electrochemical or chemical formation of nickel hydrated oxides on a working nickel oxide electrode surface with oxidation state greater than two. This pretreatment consists of an operation by which the nickel oxide surface is modified to its reactive state so that when it contacts the sample containing the solute it will undergo a characteristic potential-time transient indicative of the sample concentration. The pretreatment operation can be done by exposing the electrode to a suitable oxidizing solution such as sodium hypochlorite (NaOCl) or by applying an oxidizing voltage to the electrode for a prescribed time period. The pretreatment in the preferred embodiment consists of potentiostatically or chemically converting the nickel oxide surface on the working electrode to another chemical form of nickel oxide. No visible physical alternation of the nickel/nickel oxide electrode occurs during pretreatment or use. The analytical measurement then consists of observing the potential-time transient (change in potential (volts) over a period of time) as the higher nickel oxide layer reacts with the solutes in the sample. Solutions of known solute concentrations are used to prepare a calibration plot such as that shown in FIG. 2. The shifts in potential are for a prescribed time interval. The corresponding shift in potential for a sample solution is converted to concentration by use of the calibration curve. Metals other than nickel, such as copper, silver, and cobalt also provide this effect. The instrument provides for the electrochemical pretreatment regime, switching to open circuit potentiometry mode, monitoring and timing the potential-time transient, and holding the final potential which constitutes the analytical signal.

These and other objects and advantages will hereinafter appear and for purposes of illustration, but not of limitation, an embodiment of the invention is shown in the accompanying drawings.

BRIEF DESCRIPTIONS OF THE DRAWINGS

FIG. 3 is a diagrammatic sketch of the apparatus employed in this invention.

Figure 1:
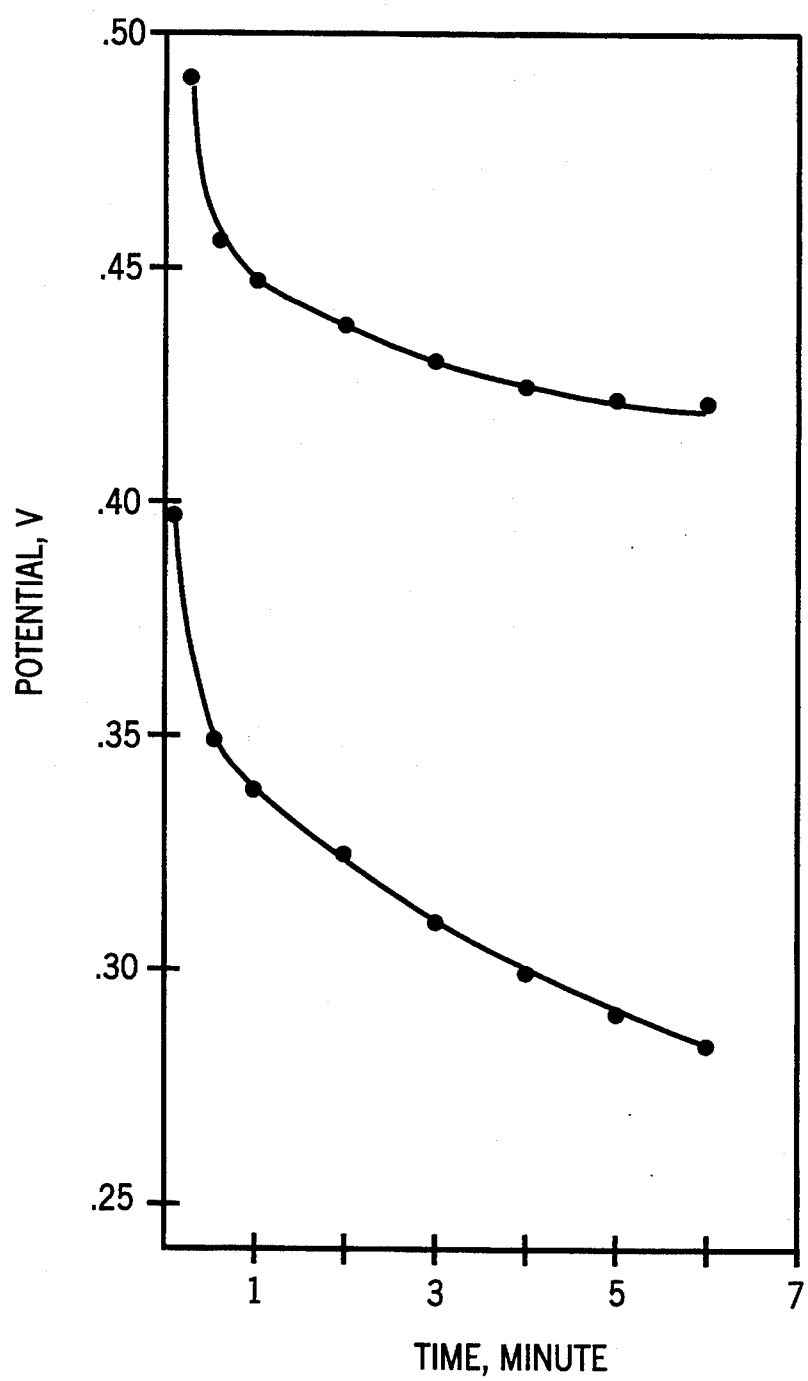
FIG. 1 is a graph showing the potential (volts.) vs. time for a 0.030M (1.4 parts per thousand) ethanol solution in water (bottom curve) compared to that for a solution containing no ethanol (upper curve).
Figure 2:
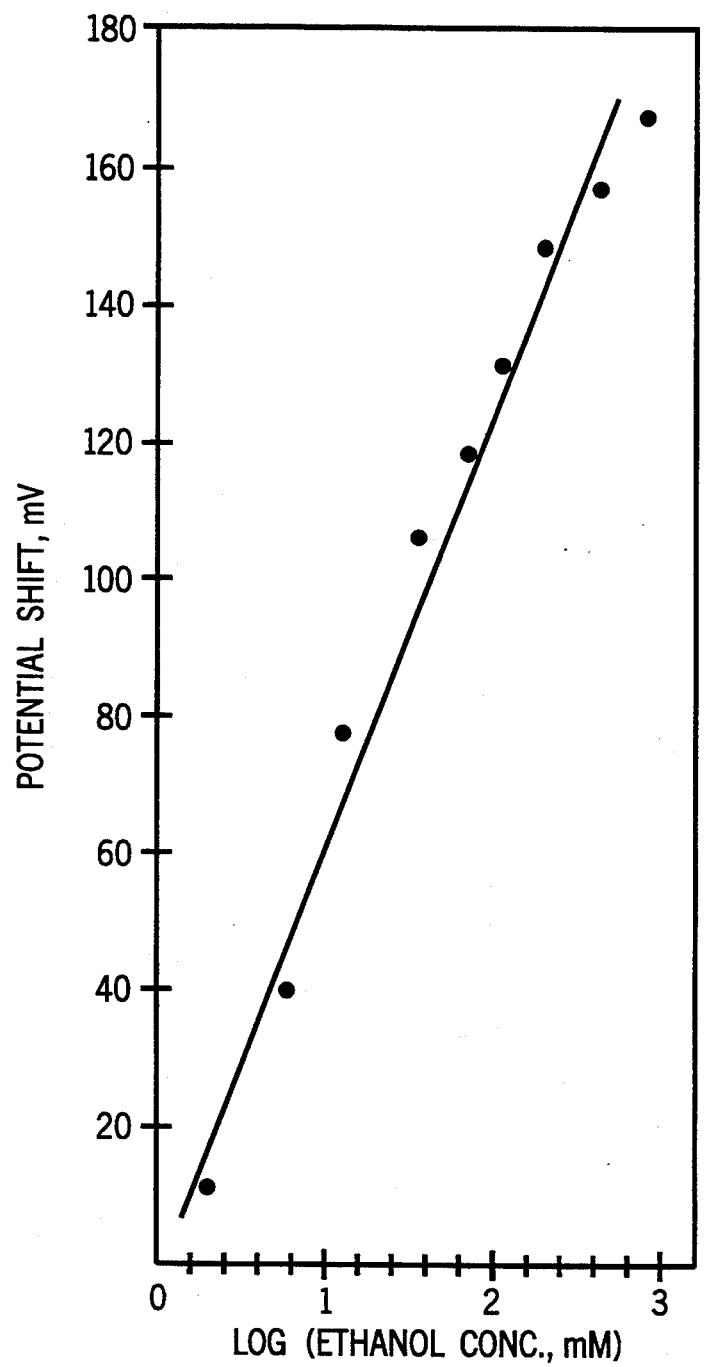
FIG. 2 is a calibration plot showing the linear relationship between log concentration and potential shift as read by the instrument for a concentration range of 100 parts per million to 46 parts per thousand water.

The following will illustrate the practice of this invention in the determination of solutes, transition and alkaline metals in solution.

DESCRIPTION OF THE PREFERRED EMBODIMENTS

EXAMPLE 1

Apparatus

Referring to FIG. 3 the working nickel oxide electrode was a planar 0.07 cm$^2$ disk embedded in Kel-F. Before use the electrode was polished using 0.3 $\mu$l alumina and rinsed with acetone and water. The reference electrode was a commercial saturated calomel electrode. The auxiliary electrode of platinum served to carry current during pretreatment. Electrochemical pretreatment of the working electrode was done potentiostatically with stirring. Alternatively, pretreatment was accomplished by immersion of the working nickel oxide electrode in stirred oxidant solution. The electrode was then transferred to the sample solutions without being allowed to dry. Potential transients were then monitored and recorded.

Reagents used were ACS Reagent Grade, except ethanol (Quantum Chemical Corporation), methanol (HPLC grade), alanine (Sigmal Chemical Co. # A-7502), surfactants and related alcohols (Aldrich). All samples and reagents were used without further purification.

Procedure

The working nickel oxide electrode was electrochemically pretreated in 0.1 molar NaOH using +0.60 V vs. SCE for 6 seconds or chemically pretreated using 5% hypochlorite or 0.4 molar persulfate for 3 minutes. The electrode package consisting of the working, auxiliary, and reference electrodes were then transferred to the sample solution which contained 0.1M NaOH and the potential-time transient was observed. The results for analytical measurements of a series of alcohols and amino acids are summarized in Table 1. The relative standard deviations for the background and analytical signals at 0.5, 5, and 60 seconds were found to be less than one percent. The data also showed the influence of the molecular structure on the potential shifts. The higher sensitivity for amino acids could be attributed to enhanced adsorption due to electrostatic attraction between the anion and the anode. Interference by chloride and calcium can readily be eliminated by excluding them during electrode pretreatment.

TABLE 1

Analytical Measurement Results

| | Potentiometry[a] | | | |
|---|---|---|---|---|
| | Sens., mV/mM | | Low limit[b] | |
| | 5 s. | 6 min. | 5 s. | 6 min. |
| ethanol | 2.4 | 5.8 | 1.0 | 0.5 |
| methanol | 2.7 | 6.1 | 1.0 | 0.5 |
| alanine | 4.0 | 9.6 | 0.5 | 0.3 |
| glycine | 6.2 | 9.7 | 0.5 | 0.3 |

[a]With deposition at 0.60 V for 5 sec.
[b]Limit of detection (mM) at S/N = 3.

The oxidized electrode was observed to retain electroactivity when exposed to the air for up to 60 seconds. The surface appeared wet throughout this period. If the surface was allowed to dry, non-reproducible signals resulted. Thus, a thin film of NaOH solution allowed retention of electrode activity so that in analytical procedures a pre-oxidized electrode can be conveniently handled and transferred between solutions if necessary. Continuous purging of the sodium hydroxide electrolyte with nitrogen gas for three minutes before preparing the higher valence oxide caused no change in the potential transients. This implied that dissolved oxygen did not influence the surface redox reactions observed here.

EXAMPLE 2

Results employing the same apparatus as furnished for Example 1 but using a flow injection analytical technique for sample handling showed that the potential transient in a flowing stream of 0.1M NaOH background electrolyte was similar to those described above. Injected 25 $\mu$l samples enhanced the potential shift so that analytical signals could be measured directly. The analytical signal was increased by only 20% when the injection volume was increased to 100 $\mu$l. The flow injection technique offers the additional advantages of smaller sample volume and convenience of sample handling. More importantly, deposition in a solution free of analyte and interferences was readily arranged. Polyoxyethylenealcohol-type nonionic surfactants yielded a remarkably large analytical signal. This response should allow the direct determinations of 10 ppm surfactant without preconcentration. In order to establish structural correlations a series of polyoxyethylate molecules and similar alcohols were examined. The results indicated a required combination of both polyoxyethylate and a long hydrocarbon for the enhanced oxidation rate. The presence of 1 mM sodium dodecyl sulfate, a representative widely used ionic surfactant, in the sample solution had no effect in the potentiometric measurement of ethanol. This was expected since neither the sulfonate nor the aliphatic part is oxidizable. Freedom from interference by this important type of surfactant is an important analytical advantage.

The presence of 10 mM sodium perchlorate, nitrate, sulfate or carbonate during the deposition process did not affect the potentiometric responses. This suggests that adsorption or exchange of the above ions was negligible.

EXAMPLE 3

When calcium was present in the electrolyte during the pretreatment step the subsequent analytical signals for ethanol were inhibited more than 20% by as little as 0.5 mole per cent calcium vs. analyte. This interference was conveniently eliminated by carrying out the deposition step in a calcium-free electrolyte or by incorporating oxalate in the electrolyte. It is speculated that during pretreatment calcium is co-precipitated into the lattice of the nickel higher valence oxide. The crystal radii for calcium and nickelous cations are similar. Neither 0.5 mM magnesium nor 0.12 mM strontium during deposition had any effects on the potentiometric signals. A calcium "poisoned" electrode was found to require dissolution of the oxide layer in dilute mineral acid in order to restore its activity. On the other hand, the calcium effect allowed the determination of calcium in solutions of constant known concentrations of oxidizable solutes. Thus, this invention allows a new method for the determination of calcium in water.

EXAMPLE 4

If during pretreatment, one millimolar chloride is present, analytical signals similar to those observed for alcohols and amino acids are also observed. Thus chloride could be determined in the absence of other reactants. The shift was attributed to complexation by chloride to stabilize the nickel higher oxidation state more than the lower oxidation state. The sensitivity of the analytical signal to chloride was about twice that for ethanol. When both 1.0 mM chloride and 1.0 mM methanol were present in the solution the combined response was additive. When other analytes are being measured, interference by chloride can conveniently be prevented by excluding chloride from the pretreatment solution.

We claim:

1. A method for determination of alcohols, amino acids, carbohydrates and calcium comprising providing an aqueous solution containing one or more of the same; pretreating a metal oxide electrode where the metal of the oxide is selected from the group consisting of nickel, copper, silver and cobalt, by applying an oxidizing voltage to the electrode for a prescribed time period, immersing the pretreated electrode in the solution and measuring the potential-time transient of the electrode and comparing the curve of resulting potential-time transient of the solution to the potential-time curve transient of a known standard solution.

2. The method of claim 1 where the aqueous solution is a flowing stream.

3. A method for determination of alcohols, amino acids, carbohydrates and calcium comprising providing an aqueous solution containing one or more of the same; pretreating a metal oxide electrode where the metal of the oxide is selected from the group consisting of nickel, copper, silver and cobalt, by immersing the electrode in a stirred oxidizing solution, immersing the pretreated electrode in the said aqueous solution and measuring the potential-time transient of the electrode and comparing the curve of the resulting potential-time transient of the said aqueous solution to the potential-time transient curve of a known standard solution.

4. The method of claim 3 where the aqueous solution is a flowing stream.

* * * * *